United States Patent [19]

Bosio

[11] 4,212,589
[45] Jul. 15, 1980

[54] DEVICE FOR PRODUCING AN ARTIFICIAL BLOOD CIRCULATION

[76] Inventor: Roberto Bosio, Via Torino 227, Castiglione Torinese (Torino), Italy

[21] Appl. No.: 944,211

[22] Filed: Sep. 20, 1978

[30] Foreign Application Priority Data

Sep. 21, 1977 [IT] Italy .............................. 69080 A/77

[51] Int. Cl.² .......................... F04B 49/06; F04B 43/06
[52] U.S. Cl. ........................................ 417/12; 417/394; 128/214
[58] Field of Search .............. 417/12, 394; 128/214 F, 128/DIG. 12

[56] References Cited

U.S. PATENT DOCUMENTS

| | | | |
|---|---|---|---|
| 2,405,734 | 3/1946 | Coe | 417/394 |
| 2,960,038 | 11/1960 | Lupfer | 417/394 |
| 3,048,121 | 8/1962 | Sheesley | 417/394 |
| 3,194,164 | 7/1965 | Fink et al. | 128/214 F |
| 3,451,347 | 6/1969 | Chimura | 417/394 |
| 3,536,423 | 10/1970 | Robinson | 417/394 |
| 4,116,589 | 9/1978 | Rishton | 128/214 F |

*Primary Examiner*—William L. Freeh
*Attorney, Agent, or Firm*—Sughrue, Rothwell, Mion, Zinn and Macpeak

[57] ABSTRACT

A pump has a tubular membrane (14) deformed cylindrically by fluid driving pressure to produce an artificial blood circulation. The pump has a feeler (42) which follows the deformation of membrane (14) and operates a switch (102) to close the circuit of an optical signalling device (103) when the deformation of the membrane (14) reaches a predetermined value. A control circuit (104) may be provided for the automatic regulation of the fluid driving pressure acting on the membrane (14) in dependence upon the duration of the closure time of the switch (102). (FIG. 7).

6 Claims, 8 Drawing Figures

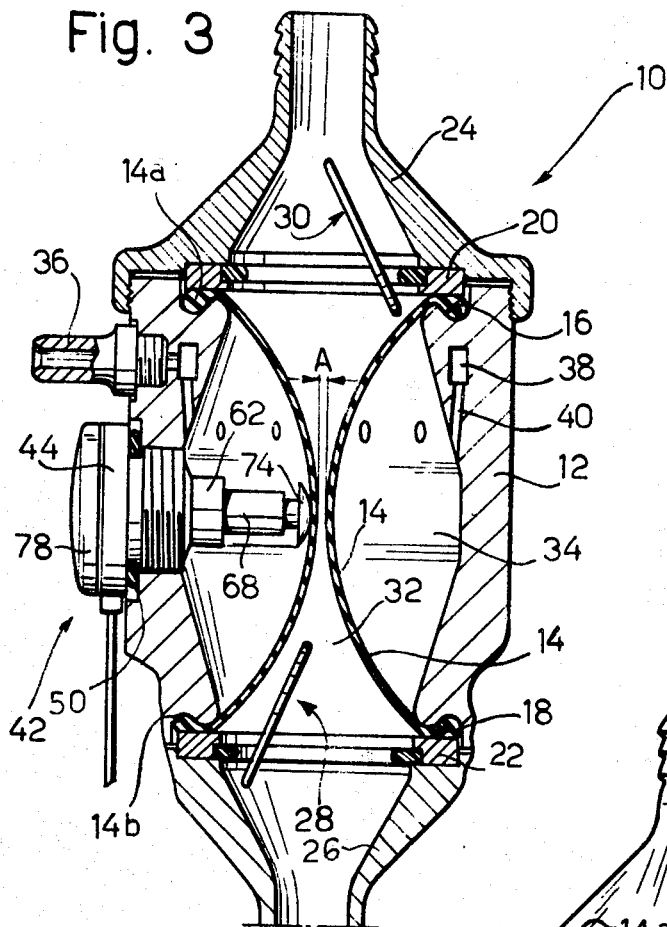
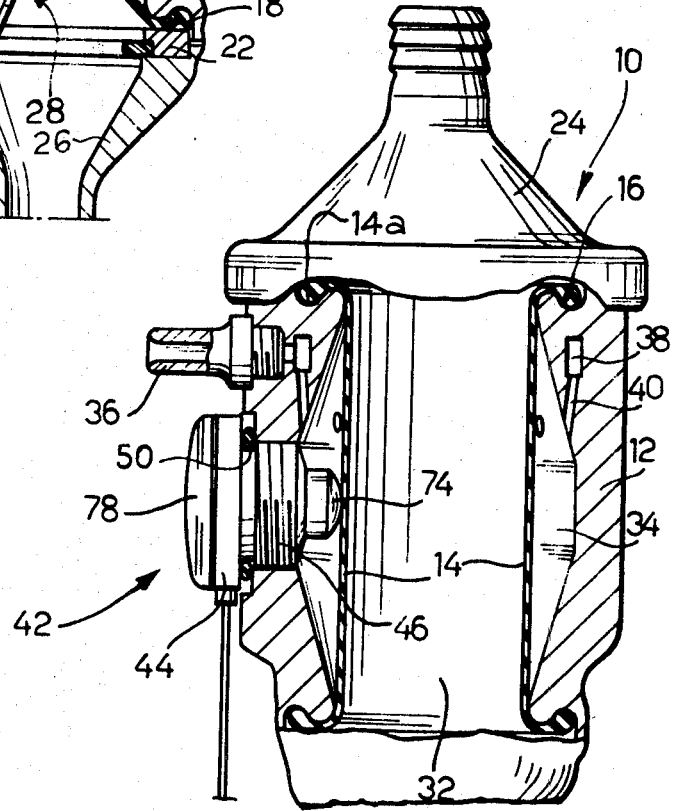

DEVICE FOR PRODUCING AN ARTIFICIAL BLOOD CIRCULATION

The present invention relates to a pump for producing an artificial blood circulation.

More particularly, the inventiom concerns a pump for producing an artificial blood circulation of the type including:

a tubular body having two end fittings with unidirectional inlet and delivery valves respectively for connection to a blood circuit, an elastically deformable tubular membrane disposed inside the tubular body and anchored at the opposite ends of the body to delimit between said ends a pumping chamber within the tubular membrane, in communication with said two end fittings, an annular chamber being defined between the tubular body and the said tubular diaphragm, means for placing said annular chamber alternately in communication with a source of driving fluid under pressure and with a source of vacuum to cause said tubular membrane to alternate cyclically between an undeformed configuration of substantially cylindrical form and a deformed condition of substantially hourglass form, and a pressure regulator to regulate the pressure of said driving fluid.

In known pumps of the aforesaid type the problem arises of adapting the pressure of the driving fluid, by means of the pressure regulator, to the continually variable flow resistance of the blood fluid in the vascular system, in order to avoid too much throttling of the tubular membrane due to the pressure of the driving fluid, in its most restricted zone, reaching a critical value such as to risk damage to the red corpuscles, with serious consequences clinically. The regulation of the driving pressure of known such pumps by means of the pressure regulator cannot be done satisfactorily since the pump operator cannot know when the deformation of the tubular membrane reaches the critical value.

On account of the aforesaid variable flow resistance of the blood fluid it is also difficult, in the case where two pumps are used to simulate an entire heart, to ensure a delivery for the left ventricle which is approximately constant and equal to that of the right ventricle.

SUMMARY OF THE INVENTION

The present invention, with a view to avoiding these problems, provides a pump of the type defined for producing an artificial blood circulation, characterised in that the pump further comprises:

a feeler supported in the tubular body of the pump for sliding movement along an axis which is substantially perpendicular to the longitudinal axis of said tubular body and is located at substantially equal distances from the ends of said tubular body; resilient means urging the inner end of the feeler into contact with the lateral surface of the tubular membrane;

a switch having fixed contact means carried by the tubular body of the pump and movable contact means carried by said feeler, said movable contact means coming into contact with said fixed contact means to close the said switch when the feeler, starting from a rest position corresponding to the undeformed configuration of the tubular membrane, has been displaced to a position corresponding to a predetermined deformation of the tubular membrane;

stop means to prevent further displacement of said feeler under the action of said resilient means after said closure of the switch, and an electrical circuit which is completed upon said closure of the switch to energise a signalling member.

By virtue of these characteristics it is possible for the pump operator to act opportunely on the pressure regulator to adapt to driving fluid pressure to the variable flow resistances of the blood fluid in such a way as to prevent the deformation of the tubular membrane from reaching the critical value.

According to a preferred embodiment of the invention, the electrical circuit also comprises:

first electrically operable control means acting on the pressure regulator to increase the regulated pressure thereof;

second electrically operable control means acting on the pressure regulator to reduce the regulated pressure thereof;

timer means operable to close the said switch, said timer means being calibratable to time an interval corresponding to the optimum duration of the closure time of the switch;

means for comparing the effective closure time of the switch with the interval timed by the timer;

means for operating automatically said first control means both in the case of shortfall in the closure of the switch during the operation of the pump, and in the case in which the closure time of the switch is less than the optimum interval timed by the timer, and means to activate said second control means automatically when the closure time of the switch exceeds the optimum interval timed by the timer.

This preferred embodiment of the invention has the advantage of ensuring automatic regulation of the driving fluid pressure in dependence upon the variable flow resistance of the blood fluid, while affording the possibility of manual intervention quickly to effect manual regulation in emergencies or when convenient.

DESCRIPTION OF THE DRAWINGS

The invention will now be described, by way of non-limiting example, with reference to the accompanying drawings, in which:

FIG. 2 is an axial section on an enlarged scale of the pump shown in FIG. 1, with the tubular membrane of the pump in the undeformed condition;

FIG. 3 is an axial section similar to that of FIG. 2 showing the tubular membrane in its deformed condition;

DETAILED DESCRIPTION OF THE ILLUSTRATED EMBODIMENTS

Figure 1:
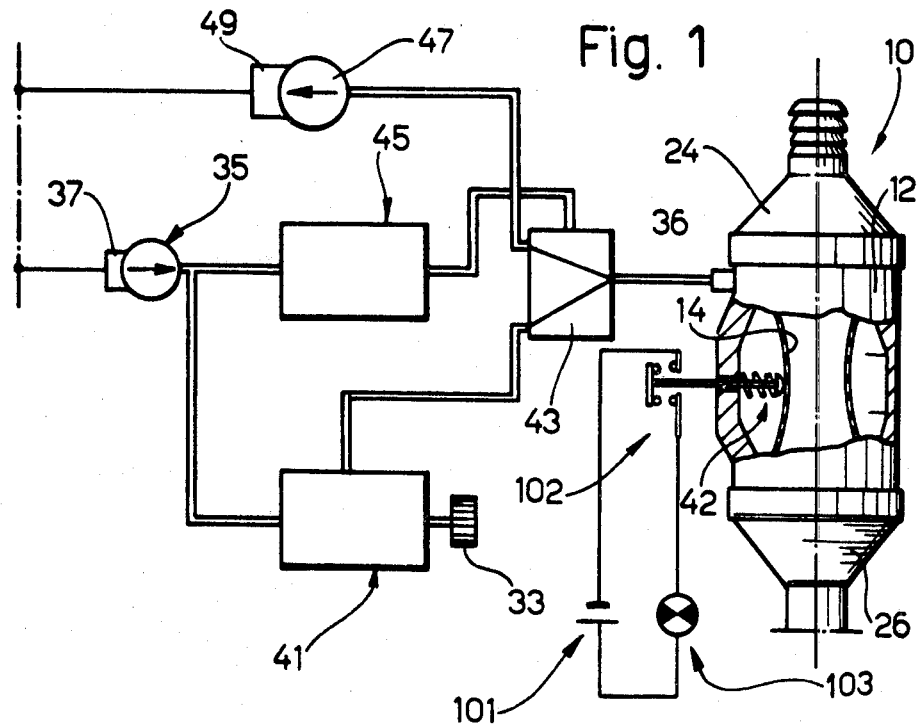
FIG. 1 shows schematically a pump and its associated electrical control circuit according to a first embodiment of the invention.

In the embodiment of FIGS. 1 to 6, reference numeral 10 shows in its entirety a pump according to the invention which may be used to simulate a ventricle of the cardiac muscle in such a way as to act as one half an artificial heart intended for extra-corporeal blood circulation, or alternatively as a complete heart, in which case the pump would be paired with another similar pump.

The pump 10 has an external rigid-walled tubular body 12 which is lined internally with an elastically deformable tubular membrane 14 provided at its ends with annular enlarged beads 14a, 14b. The opposite end faces of the tubular body 12 are formed with two annular grooves 16, 18 in which the annular beads 14a, 14b of the tubular membrane 14, are located. The said beads 14a, 14b are compressed and retained in the grooves 16, 18 by respective heads 20, 22 of flat disc form which are clamped to the opposite ends of the body 12 by end fittings 24 and 26 secured to the ends of the body. Respective unidirectional inlet and outlet valves 28 and 30 are carried by the heads 20 and 22 respectively.

The interior of the tubular membrane 14 forms a central pump chamber 32 communicating with the two end fittings 24 and 26. An annular control chamber 34 is defined between the tubular body 12 and the tubular membrane 14.

The internal surface of the wall of the tubular body 12 has in cross section a substantially elliptical shape with its major axis in the plane of FIGS. 2 and 3, the cross sectional area delimited by the said internal surface increasing from the ends towards the central part so as to increase, for given external dimensions, the useful volume of pump 10 and thence the dose of blood fluid which is delivered in each operative cycle of the pump.

A driving fluid under pressure is admitted cyclically into the annular control chamber 34 under control of a control circuit (FIG. 1) which includes a compressor 35 driven by an electric motor 37. The coompressor 35 delivers the driving fluid, through an adjustable pressure regulator 41, to a three-way fluid valve 43. The pressure regulator 41 is fitted with a control knob 33 which is rotatable in opposite rotational senses in order to increase or decrease the pressure of the control fluid delivered to the valve 43.

The three-way fluid valve 43 is controlled by a fluid pressure pulse generator 45, connected to the compressor, 35, which operates the valve 43 cyclically so as to connect the control chamber 34 of the pump alternately to the compressor 35 via the pressure regulator 41, and to a vacuum pump 47 which is driven by an electric motor 49.

The driving fluid under pressure delivered from the valve 43 is admitted into the annular chamber 34 through a connector 36 fixed to the wall of the tubular body 12 and connected within said wall to an annular duct 38. A number of distributor channels 40 communicate with the duct 38 and lead into the control chamber 34 at a number of points distributed around the perimeter of the body 12.

A tubular housing 44 of plastics material has an external screw thread 46 by means of which it is fitted into a threaded hole 48 in the side wall of the tubular body 12, substantially equidistantly from the ends of said body. An elastic sealing ring 50 affords a fluid-tight seal between the housing 44 and the side wall of the tubular body 12. The housing 44 is formed with a through bore having three coaxial bore portions 52, 54 and 56, proceeding from the inside to the outside of the bore, of increasing diameter, two annular radial shoulders 58 and 60 being defined between the bore portions 52, 54 and 54, 56 respectively.

Reference numeral 42 indicates generally a feeler which is slidable in the housing 44 along an axis which is perpendicular to the longitudinal axis of the tubular body 12. The feeler 42 (FIG. 5) has two tubular coaxial elements 62, 68, telescopically slidable one within the other.

The larger diameter tubular element 62 is of metal and is axially slidable in the innermost bore portion 52. The tubular element 62 is provided at its inner end within the housing 44 with an external annular flange 64 and at its outer end with a land 66 having a cylindrical internal surface.

The smaller diameter tubular element 68 is telescopically slidable within the internal cylindrical surface of the land 66 of the metal tubular element 62. The tubular element 68 is of plastics material and is provided at its inside end with an external annular flange 70 and at its outer end with a head 74 having a threaded stem 72 which is screwed into the said outer end. The head 74 has a curved outwardly convex profile.

The housing 44 is provided at its outer end with an externally threaded cylindrical wall 76 onto which a cap 78 is screwed with an interposed elastic sealing ring 80. The cap 78, of plastics material, is formed with a central axially extending internal stem 82 serving for the support and centering of a first helical compression spring 84 which is interposed between the internal wall of the cap 78 and the threaded stem 72 of the head 74.

A second helical compression spring 86 is interposed between the external annular flange 64 of the tubular metal element 62 and the radial annular shoulder 58 of the housing 44.

Two metal pins 88 and 90 (FIG. 6) which act as fixed contacts project radially inwardly towards the interior of the housing bore portion 56 into the path of movement of the external annular flange 64 of the tubular metal element 62. The fixed contact pins 88, 90 are both electrically connected to an electrical conductor 92 which is supported in an electrically insulating threaded bush 94 which is screwed into a tubular boss 96 of the housing 44. An elastic O-ring 98 is interposed between the bush 94 and an annular spacer 100 to ensure a fluid-tight seal between the exterior and the interior of the housing 44. The external annular flange 64 of the tubular metal element 62 acts as a movable contact and cooperates with the fixed contact pins 88, 90, forming in effect a switch, indicated generally by 102 in FIG. 1, inserted in an electrical control circuit. The control circuit further includes a current source 101 such as a battery and a lamp 103.

OPERATION

The operation of the pump illustrated in FIGS. 1 to 6 will now be described.

Figure 4:
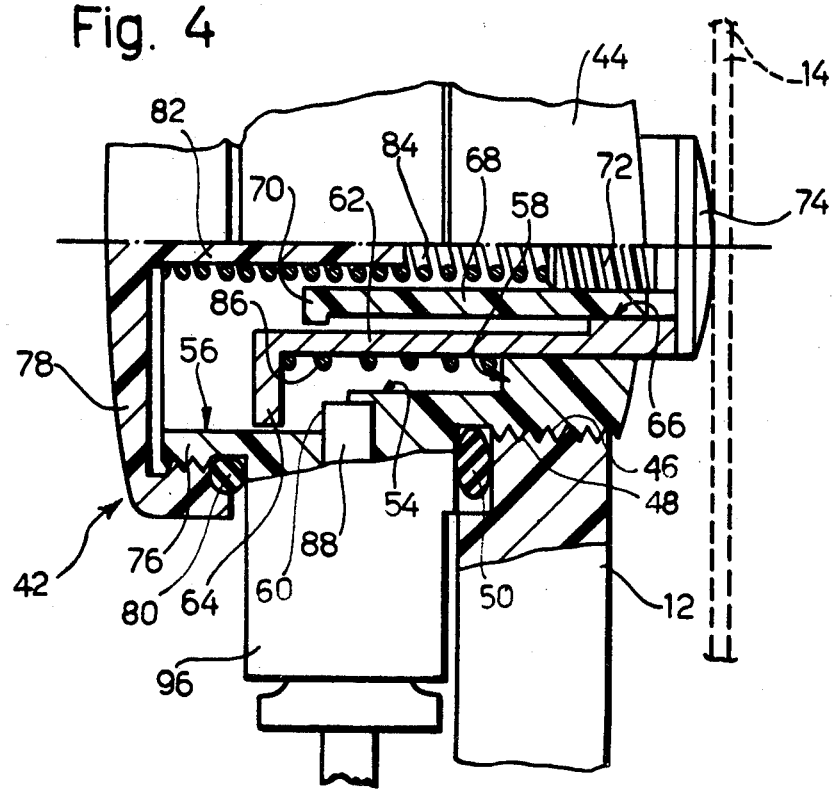
FIG. 4 is a partly cut away axial section on a further enlarged scale of part of the pump in the condition shown in FIG. 2.
Figure 5:
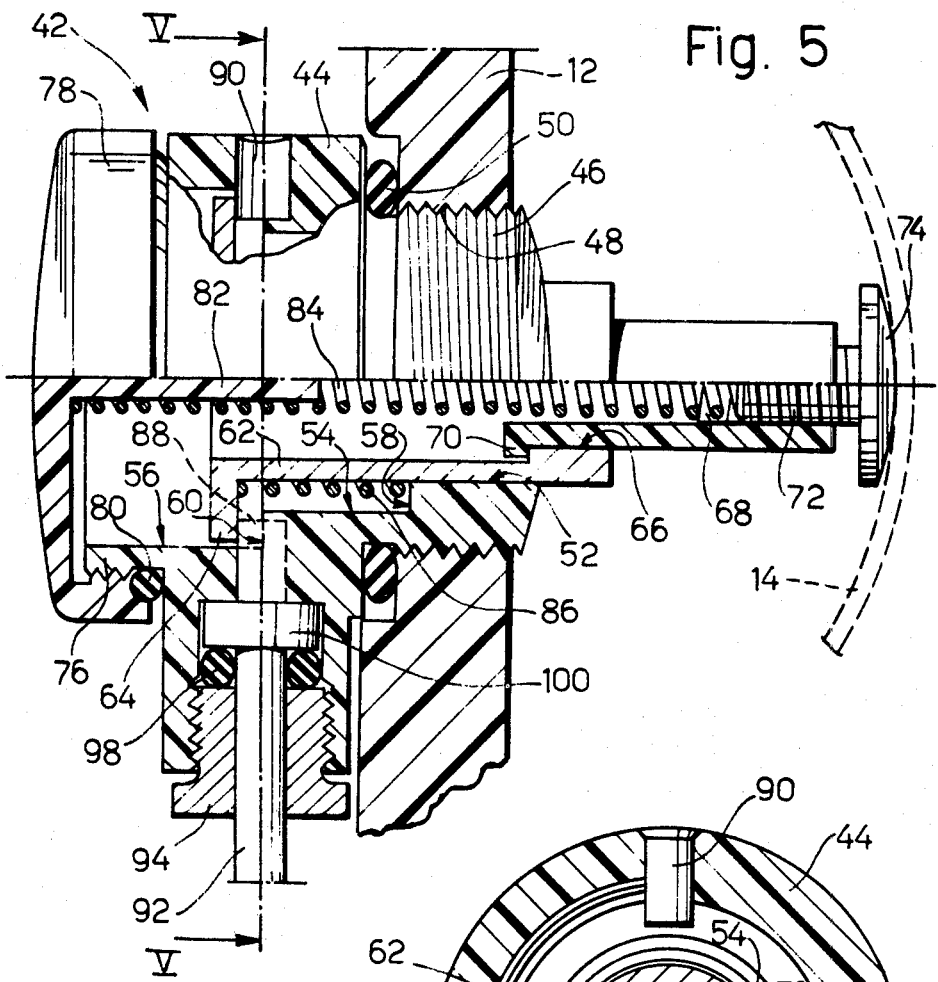
FIG. 5 is a section similar to that of FIG. 4 of part of the pump in the condition shown in FIG. 3.
Figure 6:
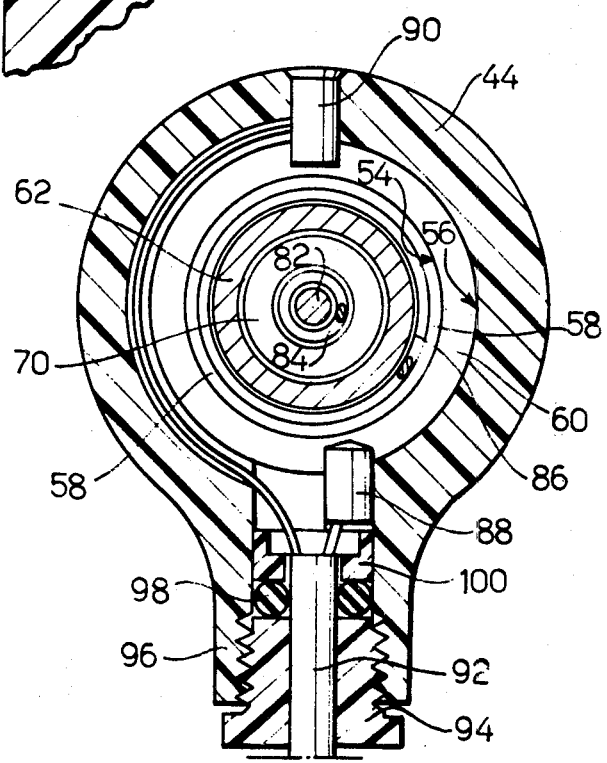
FIG. 6 is a cross-section taken on line VI—VI of FIG. 5.

In the position illustrated in FIGS. 2 and 4, the tubular membrane 14 is in an undeformed condition, having a substantially cylindrical shape. This corresponds to the induction position in which the pumping chamber 32 is full of blood fluid drawn in through the inlet valve 28. In this position the feeler 42 in in a rest position, the tubular plastics element 68 being retracted and the first spring 84 being loaded so as to maintain the head 74 in contact with the tubular membrane 14. The tubular metal element 62 is also retracted, unloading the second helical spring 86, which has a stiffness or spring rate less than that of the first spring 84.

An operating cycle commences when the pulse generator 45 delivers a pulse causing the fluid valve 43 to adopt the position in which the connector 36 is connected to the compressor 35 through the pressure regulator 41. Driving fluid under pressure is then admitted into the annular control chamber 34, causing a progressive inward deformation of the tubular membrane 14, which in turn causes blood fluid contained in the pump chamber 32 to be expelled through the outlet valve 30.

During the progressive inward deformation of the tubular membrane 14 the head 74 of the feeler 42 is maintained in contact with the said membrane 14 by the thrust of the first spring 84. This ensures a progressive extension of the tubular plastics element 68 towards the axis of the body 12 relative to tubular element 62, until the external annular flange 70 of the tubular metal element 68 engages the inner end of the land 66 of the tubular metal element 62. Upon further inward deformation of tubular membrane 14, the tubular metal element 62 is drawn by the tubular element 68, withdrawing the element 62 progressively from the housing 44. Such displacement of the tubular metal element 62 causes the external annular flange 64 of the element 62 to approach the annular shoulder 58 of the housing 44, loading the second spring 86. The withdrawal of the tubular metal element 62 from the housing 44 is arrested when the external annular flange 64 engages the fixed contact pins 88 and 90 thus causing the closure of the switch 102 and the illumination of the lamp 103. In this position (FIGS. 3 and 5) the feeler 42 is in its condition of maximum excursion towards the axis of the tubular body 12, corresponding to a deformation of the tubular membrane 14 into substantially an hourglass shape, forming a constriction or throttle having a minimum flow cross section indicated by A in FIG. 3.

By means of a series of initial calibrating cycles the depth to which the stem 72 of the head 74 is screwed into the tubular element 68 is adjusted in such a way that the stroke effected by the feeler 42 in order to close the switch 102 corresponds to a predetermined safety value of the throttle cross section A of the membrane 14.

The pumping cycle ends when the three-way fluid valve 43, piloted by the pulse generator 45, places the annular control chamber 34 in communication with the vacuum pump 47, causing the tubular membrane 14 to expand and return to the initial undeformed condition. During this induction stroke the tubular element 68 of the feeler 42 is returned to the rest position shown in FIG. 4, and blood fluid is drawn into the pump chamber 32 through the inlet valve 28. The second spring 86 returns the tubular metal element 62 to the rest position, opening the switch 102.

Pump 10 is operating under optimum working conditions when the closure time of the switch 102, and thence the illumination time of the lamp 103, corresponds to an optimum time predetermined as a function of the frequency of the pulses provided by the pulse generator 45. The said optimum switch closure time is determined experimentally for each patient and in practice would be between 0.1 seconds and 2 seconds.

In the case where lamp 103 remains extinguished, or lights up for a lesser time than the optimum time, the operator can adjust the pressure regulator 41 by means of the control knob 33 to increase the driving fluid pressure in such a way as to bring the working of the pump 10 back to optimum conditions.

In the case where the lamp 103 remains lit for a time exceeding the optimum time the operator, warned of the danger by the long illumination time of lamp 103, can restore optimum working conditions by operating the control knob 33 of the pressure regulator 41 in the opposite sense to decrease the pressure of the driving fluid.

Figure 7:
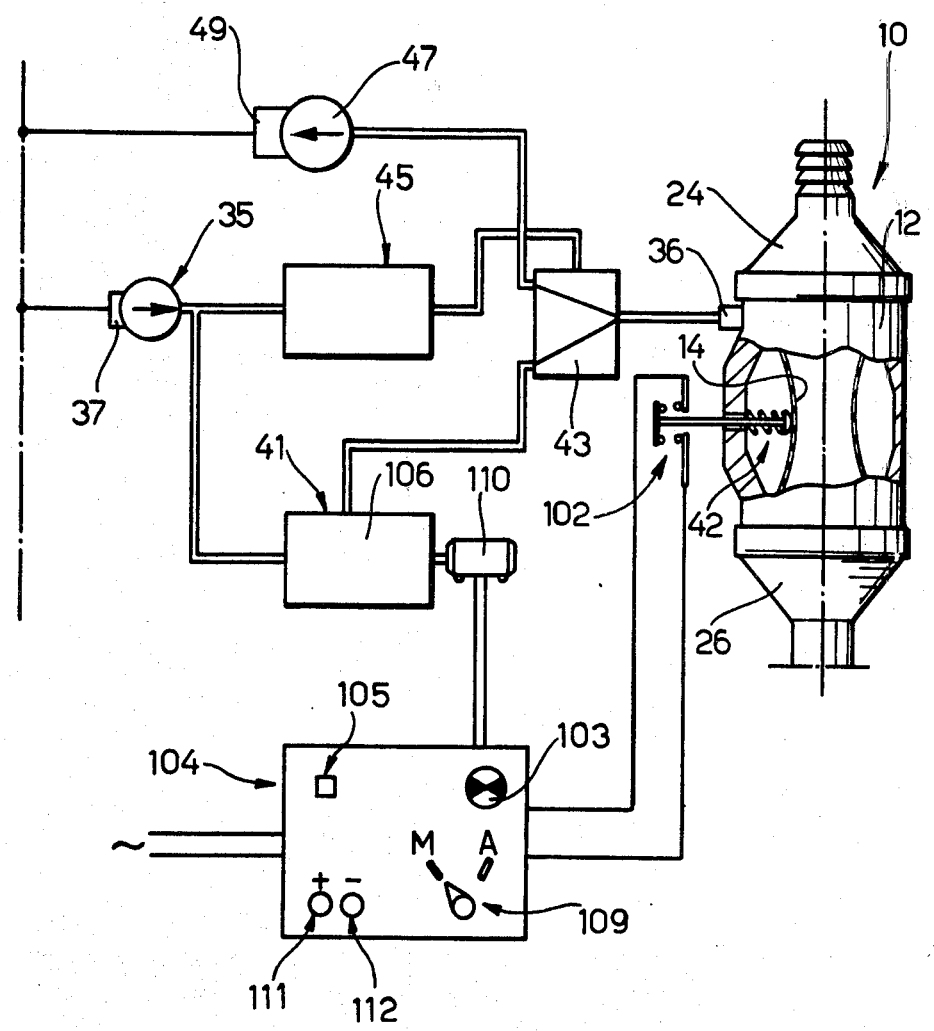
FIG. 7 shows schematically a pump and its associated electrical control circuit according to a variant of the circuit shown in FIG. 1.
Figure 8:
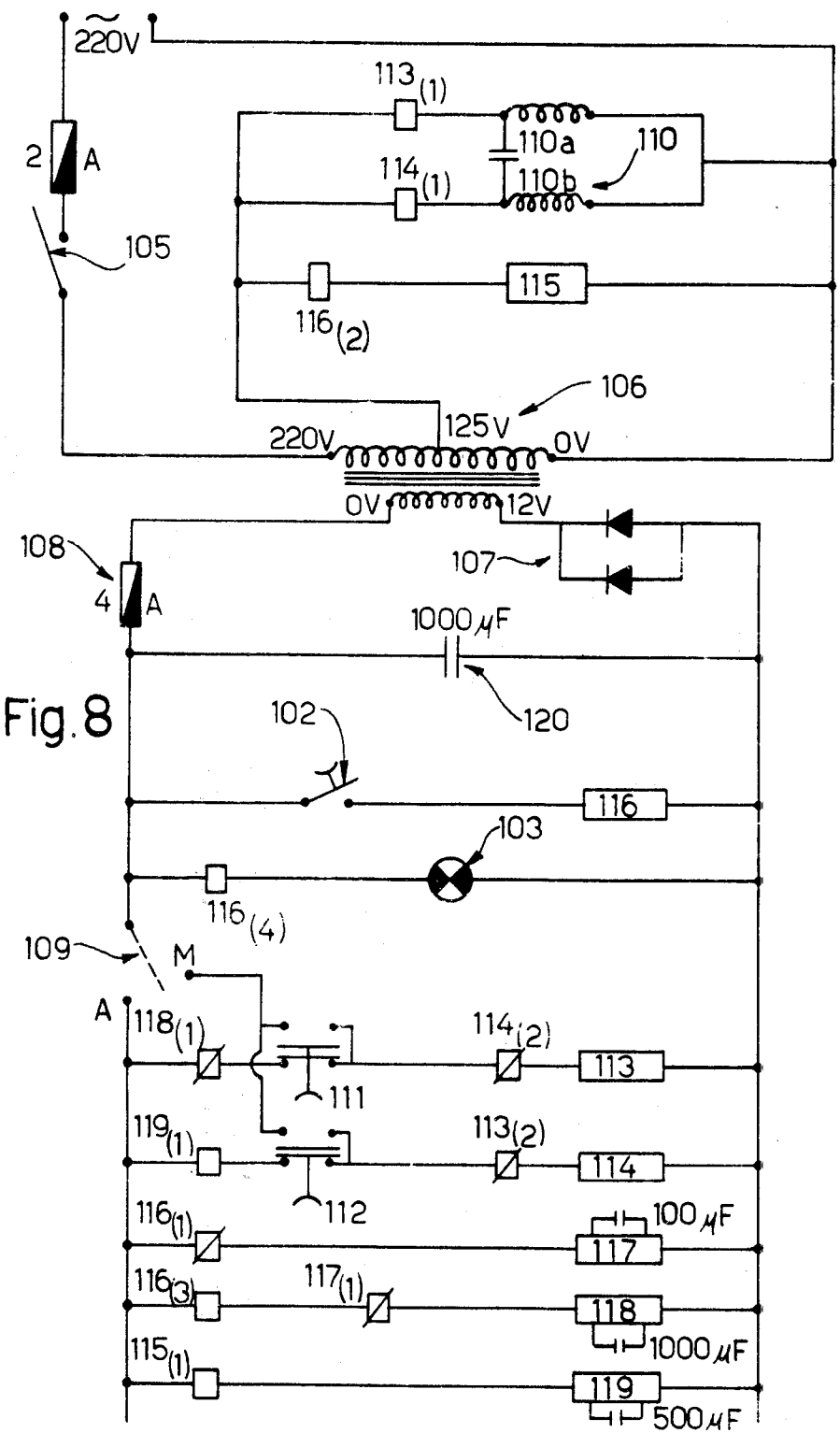
FIG. 8 is an electrical circuit diagram of the control circuit shown in FIG. 7.

In the variant illustrated in FIGS. 7 and 8, in which parts common to the embodiment of FIGS. 1 to 6 are indicated with the same reference numerals, the pump 10 is provided with a control unit, indicated generally 104, which can be preset for manual or automatic control of the pressure regulator 41 in dependence upon the operating conditions of the pump.

As seen in the electric circuit diagram of FIG. 8, the control unit 104 has a master switch 105 through which 220 volt mains alternating current may be supplied to a transformer 106. The secondary of the transformer 106 is connected to a rectification and stabilisation circuit formed by two silicon diodes 107 and a capacitor 120, and protected by a four-amp fuse 108, supplying direct current at 12 volts.

A selector switch 109 has a movable contact with two positions M and A corresponding respectively to manual and automatic operation of the pump.

The control unit 104 acts directly on a reversible electric motor 110 incorporating a speed reducer which is coupled to an adjusting element of the pressure regulator 41. As shown in FIG. 8 by way of example, the motor 110 has two field windings 110a and 110b which can be energised selectively to cause rotation of the motor in opposite directions. The control unit 104 also includes two pushbuttons 111 and 112 serving for the manual regulation of the driving fluid pressure as described below.

Manual operation

The selector switch 109 is set in position M. The operator can then control the operation of the pump, as described with reference to FIG. 1, by observing the lamp 103. The illumination of lamp 103 is in this embodiment controlled by contacts 116(4), normally open, of a relay 116 which is energised when the switch 102 is closed.

If lamp 103 remains unlit or if the duration of its illumination is less than the optimum illumination time, the operator presses the pushbutton 111 to energise a relay 113, which closes normally open contacts 113(1) supplying current to the motor winding 110a. The motor 110 then acts on the pressure regulator 41 in a sense to increase the driving fluid pressure.

If the duration of the illumination of the lamp 103 exceeds the illumination time, the operator presses the push button 112 to energise a relay 114 which closes normally open contacts 114(1), supplying current to the motor winding 110b. The motor 110 then acts on the pressure regulator 41 in a sense to decrease the driving fluid pressure. Normally closed contacts 114(2) of the relay 114 are connected in the energising circuit of the relay 113, and normally closed contacts 113(2) of the relay 113 are connected in the energising circuit of the relay 114 to serve as reciprocal safety devices to avoid completely erroneous operations by preventing simultaneous energisation of both relays 113, 114.

Automatic operation

The selector switch 109 is set in position A. The control unit 104 then effects a comparison between the duration of the closure time of the pump-operated switch 102 and an optimum time, predetermined in a series of initial calibrating cycles, set into timer 115. The timer 115 is capable of being set to time an interval between 0.1 seconds and 2 seconds and is activated by energisation of the relay 116.

If the pump-operated switch 102 remains open the relay 116 remains de-energised. The relay 116 has normally closed contacts $116_{(1)}$ in series with a relay 117, which is thus energised. Normally closed contacts $117_{(1)}$ of relay 117, placed in series with a relay 118, therefore de-energise the relay 118. The relay has normally closed contacts $118_{(1)}$ in series with the relay 113, so that the latter is energised, closing its normally open contacts $113_{(1)}$ and thereby causing excitation of the motor winding 110a. The motor 110 therefore acts upon the pressure regulator 41 in the sense of increasing the pressure of the driving fluid. The gradual increase of pressure in the pump chamber 32 due to successive diastoles and systoles causes a progressive displacement of feeler 42 until it reaches the optimum position at the end of each pumping stroke predetermined by the calibration. When this occurs, the switch 102 is closed at the end of each operating cycle of the pump, resulting in energisation of the relay 116 for a very short time. This could lead to instability in the control of the driving pressure of the pump, since rhythmic and oscillating increases in pressure could result. In order to avoid this, a 100 $\mu$F capacitor is placed in parallel with the relay 117 so as to cause a further increase in pressure until the relay 116 remains energised for a time which is neither below nor above that metered by timer 115, which is activated by closure of normally open contacts $116_{(2)}$ of the relay 116.

The energisation of the relay 116 upon each closure of the switch 102 also closes normally open contacts $116_{(3)}$ arranged in series with the relay 118, causing energisation of the latter. A 100 $\mu$F capacitor in parallel with the relay 118 keeps this relay 118 energised until the following closure of the switch 102. In this case there is no increase in pressure because the relay 118 has normally closed contacts $118_{(1)}$ in series with the relay 113, so that the control of the pump becomes stable.

If the duration of the closure time of the pump-operated switch 102 (corresponding to the duration of the energisation of the relay 116) exceeds the preset time of the timer 115, then normally open contacts $115_{(1)}$, associated with the timer 115, arranged in series with a relay 119, are closed at the end of the interval timed by the timer 115, causing energisation of the relay 119. The relay 119 has normally open contacts $119_{(1)}$ in series with the relay 114, so that the relay 114 is energised, thereby exciting the motor winding 110b through the contacts $114_{(1)}$. The motor 110 thereupon operates the pressure regulator 41 in a sense to decrease the driving fluid pressure, returning the pump 10 to the optimum conditions of operation.

In this case also, in order to avoid instability in the driving pressure control, resulting in a rhythmic and oscillating decrease in pressure, a 500 $\mu$F capacitor is placed in parallel with the relay 119, so as to cause further progressive decrease in the driving pressure until the duration of the closure time of the switch 102 is returned to the optimum value.

In the case in which there is an unforeseen variation in the condition of the patient, a supervising operator can intervene immediately by returning the switch 109 to the 'manual' position M and then reverting to manual control by means of the pushbuttons 111 and 112, as previously described.

The indicator lamp 103 may be replaced by any other type of optical or acoustic indicating or signalling means.

In the case in which it is desired to produce a complete artificial heart for extra-corporeal blood circulation two pumps according to the invention may be employed, arranged in parallel and each equipped with its own regulation system.

What is claimed is:

1. Pump for producing an artificial blood circulation of the type comprising:
    a tubular body having end fittings for connection to a blood circuit,
    unidirectional inlet and outlet valves in respective end fittings,
    an elastically deformable tubular membrane, located within the tubular body and fixed to the latter at its two ends to define a pumping chamber within the tubular membrane, in communication with the two said end fittings, and to define an annular control chamber between the tubular body and the said tubular membrane;
    means for placing said annular control chamber alternately in communication with a source of driving fluid under pressure and with a source of lower pressure to deform the tubular membrane cyclically between an undeformed substantially cylindrical shape and a deformed substantially hourglass shape and vice versa, and
    a pressure regulator for regulating the pressure of the driving fluid,
    wherein the improvements reside in the further provision of:
    a feeler supported in the tubular body of the pump for sliding movement along an axis which is substantially perpendicular to the longitudinal axis of said tubular body and is located at substantially equal distances from the ends of said tubular body;
    resilient means urging the inner end of the feeler into contact with the outer surface of the tubular membrane;
    a switch having fixed contact means carried by the tubular body of the pump and movable contact means carried by said feeler, said movable contact means coming into contact with said fixed contact means to close the said switch when the feeler, starting from a rest position corresponding to the undeformed configuration of the tubular membrane, has been displaced to a switch closure position corresponding to a predetermined deformation of the tubular membrane;
    stop means to prevent further displacement of said feeler under the action of said resilient means after said closure of the switch
    an electrical circuit which is completed upon said closure of the switch, and
    a signalling member in said electrical circuit which is energised upon closure of said switch 2. Pump as claimed in claim 1, wherein the signalling member comprises a lamp.

3. Pump as claimed in claim 1, wherein regulating means are provided to vary the length of the stroke of the feeler from said rest position to the switch closure position.

4. Pump as claimed in claim 1, including an electrically insulating housing in which the feeler is supported slidably, the housing being located in the side wall of the tubular body of the pump.

5. Pump as claimed in claim 4, wherein the feeler comprises:
- a first tubular element of electrically conductive material slidable within the housing;
- a second tubular element of electrically insulating material slidable telescopically within the first tubular element and carrying, at an outer end facing towards the tubular membrane, a head with a convex surface which rests on the external surface of the tubular membrane;
- a first external annular flange at the end of the first tubular element within the housing;
- a first helical compression spring, coaxial with the said two tubular elements, reacting at one end against an end wall of the housing and at the other end against said outer end of said second tubular element;
- a second helical compression spring interposed between said annular flange and part of the housing, said first helical spring having a stiffness or spring rate greater than that of the second spring;
- a pair of fixed contacts extending radially inwardly towards the axis of the housing and disposed in the path of displacement of the said first flange of the first tubular element to limit displacement of said first tubular element towards the axis of the tubular body;
- a second external annular flange at the end of the second tubular element remote from said head;
- a land on the internal surface of the first tubular element which is engaged by the said second annular flange to limit the outward displacement of the second tubular element relative to the first tubular element.

6. Pump as claimed in claim 1, wherein the said electrical circuit further comprises:
- first electrically operable control means acting on the pressure regulator to increase the regulated pressure thereof;
- second electrically operable control means acting on the pressure regulator to reduce the regulated pressure thereof;
- timer means operable to close said switch, said timer means being calibratable to time an interval corresponding to the optimum duration of the closure time of the switch;
- means for comparing the effective closure time of the switch with the interval timed by the timer;
- means for operating said first control means automatically, both in the case of shortfall in the closure of the switch during the operation of the pump and in the case in which the closure time of the switch is less than the optimum interval timed by the timer, and
- means for operating said second control means automatically when the closure time of the switch exceeds the optimum interval timed by the timer.

* * * * *